United States Patent [19]

Ueda et al.

[11] Patent Number: 4,591,590

[45] Date of Patent: May 27, 1986

[54] BENZHYDRYLPIPERAZINE DERIVATIVES, PROCESSES FOR THE PREPARATION THEREOF AND PHARMACEUTICAL COMPOSITION COMPRISING THE SAME

[75] Inventors: Ikuo Ueda, Toyonaka; Daizo Morino, Matsubara; Koichi Takimoto, Takarazuka, all of Japan

[73] Assignee: Fujisawa Pharmaceutical Co., Ltd., Osaka, Japan

[21] Appl. No.: 563,756

[22] Filed: Dec. 21, 1983

[30] Foreign Application Priority Data

Dec. 24, 1982 [JP] Japan .................. 57-231855

[51] Int. Cl.$^4$ .................. C07D 401/12; A61K 31/495
[52] U.S. Cl. .................. 514/252; 544/360; 544/368; 544/396; 514/253; 514/255
[58] Field of Search .................. 544/360, 396, 368; 424/250; 514/252, 253, 255

[56] References Cited

U.S. PATENT DOCUMENTS

| | | | |
|---|---|---|---|
| 2,861,072 | 11/1958 | Weston et al. .................. | 544/396 |
| 3,244,718 | 4/1966 | Biel .................. | 544/396 |
| 4,199,582 | 4/1980 | Oka et al. .................. | 544/396 |
| 4,243,806 | 1/1981 | Raeymaekers et al. .................. | 544/360 |

FOREIGN PATENT DOCUMENTS

| | | | |
|---|---|---|---|
| 649848 | 12/1964 | Belgium .................. | 544/360 |
| 0000758 | 2/1979 | European Pat. Off. .................. | 544/396 |
| 58146 | 8/1982 | European Pat. Off. .................. | 544/396 |
| 97340 | 1/1984 | European Pat. Off. .................. | 544/396 |
| 2024350 | 11/1970 | Fed. Rep. of Germany .................. | 544/396 |
| 763609 | 3/1971 | France .................. | 544/396 |
| 7493379 | 5/1974 | Japan . | |
| 1184714 | 3/1970 | United Kingdom .................. | 544/360 |
| 1279843 | 5/1970 | United Kingdom .................. | 544/396 |
| 1241263 | 8/1971 | United Kingdom .................. | 544/360 |
| 1280290 | 7/1972 | United Kingdom .................. | 544/396 |
| 1598278 | 9/1981 | United Kingdom .................. | 544/360 |

OTHER PUBLICATIONS

Chemical Abstracts, vol. 82, No. 23, Jun. 9th, 1975, p. 618, No. 156367d, Columbus Ohio (USA).

*Primary Examiner*—George F. Lesmes
*Assistant Examiner*—S. A. Gibson
*Attorney, Agent, or Firm*—Oblon, Fisher, Spivak, McClelland & Maier

[57] ABSTRACT

The present invention relates to novel benzhydrylpiperazine derivatives having anti-allergic activities, the preparation of these derivatives, pharmaceutical compositions comprising the same, and to a method of using these compounds therapeutically in the treatment of allergic symptoms in human beings and animals.

These benzhydrylpiperazine derivatives have the follow formula:

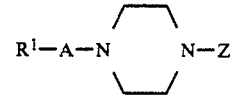

wherein A is a lower alkylene,
Z is a benzhydryl optionally substituted with halogen, and
$R^1$ is amino, aryl, pyridyl, acyl or acylamino, in which the aryl group and pyridyl group are substituted with nitro, amino or acyl amino groups, provided that Z is benzhydryl substituted with a halogen, when $R^1$ is an amino group.

9 Claims, No Drawings

BENZHYDRYLPIPERAZINE DERIVATIVES, PROCESSES FOR THE PREPARATION THEREOF AND PHARMACEUTICAL COMPOSITION COMPRISING THE SAME

The present invention relates to novel benzhydrylpiperazine derivatives and pharmaceutically acceptable salts thereof. More particularly, it relates to novel benzhydrylpiperazine derivatives and pharmaceutically acceptable salts thereof which have antiallergic activities, to processes for the preparation thereof, to pharmaceutical composition comprising the same, and to a method of using the same therapeutically in the treatment of allergic symptoms in human being and animals.

Accordingly, it is one object of the present invention to provide benzhydrylpiperazine derivatives and pharmaceutically acceptable salts thereof, which are useful as antiallergic agents.

Another object of the present invention is to provide processes for the preparation of benzhydrylpiperazine derivatives and pharmaceutically acceptable salts thereof.

A further object of the present invention is to provide pharmaceutical composition comprising, as an active ingredient, said benzhydrylpiperazine derivative or its pharmaceutically acceptable salt.

Still further object of the present invention is to provide a method of using said benzhydrylpiperazine derivative or its pharmaceutically acceptable salt in the treatment of allergic symptoms in human being and animals.

Some benzhydrylpiperazine derivatives having antiallergic activity have been known as described, for example, in European Pat. No. 32058 and U.S. Pat. No. 3,956,328.

And some benzhydrylpiperazine derivatives having similar chemical structure to the object compounds of this invention have been known as described, for example, in Japanese Laid Open Publication (KOKAI) No. 93379/1974, while it has not been known that these compounds possess antiallergic activity.

The object benzhydrylpiperazine derivatives of the present invention are novel and can be represented by the following formula [I]:

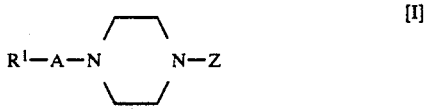

wherein A is lower alkylene,
Z is benzhydryl optionally substituted with halogen, and
$R^1$ is amino, aryl, pyridyl, acyl or acylamino, in which aryl group and pyridyl group are substituted with nitro, amino or acylamino, provided that Z is benzhydryl substituted with halogen, when $R^1$ is amino.

The object compounds represented by the above formula [I] may include stereoisomers due to asymmetric carbon atoms in the molecule, and all of such isomers are included within the scope of the invention.

In the above formula [I], suitable lower alkylene for A may be a straight or branched ($C_1$–$C_6$)alkylene group such as methylene, ethylene, propylene, trimethylene, tetramethylene, pentamethylene, hexamethylene or the like.

The halogen moiety of the benzhydryl optionally substituted with halogen for Z may include chlorine, bromine, iodine and fluorine. Suitable examples of the benzhydryl group substituted with halogen atom(s) may be 4-chlorobenzhydryl, 2-bromobenzhydryl, 2,4-dichlorobenzhydryl, 4,4'-dichlorobenzhydryl or the like.

Suitable aryl for $R^1$ may be phenyl, tolyl, xylyl, mesityl, naphthyl or the like, and the most preferable one is phenyl.

Suitable acyl for $R^1$ may include aliphatic acyl, aromatic acyl, heterocyclic acyl, and aliphatic acyl substituted with aromatic group or heterocyclic group.

Suitable examples of said aliphatic acyl may be saturated or unsaturated, acyclic or cyclic ones such as lower alkanoyl [e.g. formyl, acetyl, propionyl, butyryl, isobutyryl, valeryl, isovaleryl, pivaloyl, hexanoyl, etc.], lower alkanesulfonyl [e.g. methanesulfonyl, ethanesulfonyl, propanesulfonyl, butanesulfonyl, etc.], lower alkoxycarbonyl [e.g. methoxycarbonyl, ethoxycarbonyl, propoxycarbonyl, butoxycarbonyl, t-butoxycarbonyl, etc.], N-(lower)alkylcarbamoyl [e.g. N-methylcarbamoyl, N-ethylcarbamoyl, N-propylcarbamoyl, etc.], lower alkoxalyl [e.g. methoxalyl, ethoxalyl, propoxalyl, etc.], lower alkenoyl [e.g. acryloyl, methacryloyl, crotonoyl, etc.], ($C_3$-$C_7$)cycloalkanecarbonyl [e.g. cyclopentanecarbonyl, cyclohexanecarbonyl, etc.] or the like. Among these aliphatic acyl groups, preferred ones are lower alkanoyl [e.g. acetyl, propionyl, etc.], lower alkanesulfonyl [e.g. methanesulfonyl, ethanesulfonyl, etc.].

Suitable examples of the aromatic acyl may be aroyl [e.g. benzoyl, toluoyl, xyloyl, etc.], arenesulfonyl [e.g. benzenesulfonyl, tosyl, etc.] or the like. Among these aromatic acyl groups, preferred one is aroyl [e.g. benzoyl, toluoyl, etc.].

Suitable examples of the heterocyclic acyl may be heterocyclic carbonyl group such as furoyl, thenoyl, nicotinoyl, isonicotinoyl, thiazolylcarbonyl, thiadiazolylcarbonyl, tetrazolylcarbonyl or the like.

Suitable examples of the aliphatic acyl substituted with aromatic group may be phenyl(lower)alkanoyl [e.g. phenylacetyl, phenylpropionyl, phenylhexanoyl, etc.], phenyl(lower)alkoxycarbonyl [e.g. benzyloxycarbonyl, phenethyloxycarbonyl, etc.], phenyl(lower)alkenoyl [e.g. cinnamoyl, etc.], phenoxy(lower)alkanoyl [e.g. phenoxyacetyl, phenoxypropionyl, etc.] or the like.

Suitable examples of the aliphatic acyl substituted with heterocyclic group may be thienylacetyl, imidazolylacetyl, furylacetyl, tetrazolylacetyl, thiazolylacetyl, 2-oxo-benzothiazolin-3-ylacetyl, thiadiazolylacetyl, thienylpropionyl, thiadiazolylpropionyl or the like.

The above-mentioned acyl groups may further be substituted with one or more suitable substituent(s). Suitable examples of such substituents may be lower alkyl [e.g. methyl, ethyl, propyl, isopropyl, butyl, pentyl, hexyl, etc.], halogen [e.g. chlorine, bromine, iodine and fluorine], lower alkoxy [e.g. methoxy, ethoxy, propoxy, isopropoxy, butoxy, pentyloxy, hexyloxy, etc.], lower alkanesulfonylamino [e.g. methanesulfonylamino, ethanesulfonylamino, etc.], lower alkylthio [e.g. methylthio, ethylthio, propylthio, isopropylthio, butylthio, pentylthio, hexylthio, etc.], nitro or the like. Suitable examples of the acyl groups having such substituent(s) may be aroyl substituted with lower alkoxy, halogen, lower alkyl and/or lower alkanesulfonylamino

[e.g. 2-(or 3- or 4-)methoxybenzoyl, 2-(methanesulfonylamino)benzoyl, 4-chlorobenzoyl, 2-methylbenzoyl, etc.], phenyl(lower)alkenoyl substituted with lower alkoxy [e.g. 3,4-dimethoxycinnamoyl, etc.] or the like.

The acylamino for $R^1$ and for the substituent on the aryl and pyridyl groups for $R^1$ may include monoacylamino and diacylamino, and said diacylamino group may also include cyclic-diacylamino group such as maleimido, phthalimido and the like. The acyl moiety of these acylamino groups can be referred to those as exemplified for the acyl group mentioned before.

Suitable pharmaceutically acceptable salts of the object compounds [I] may include an inorganic acid addition salt [e.g. hydrochloride, hydrobromide, sulfate, phosphate, etc.], an organic acid addition salt [e.g. oxalate, maleate, lactate, tartrate, fumarate, methanesulfonate, benzenesulfonate, toluenesulfonate, etc.], a salt with an amino acid [e.g. aspartic acid salt, glutamic acid salt, etc.] and the like.

The object compound [I] of this invention can be prepared by the following processes.

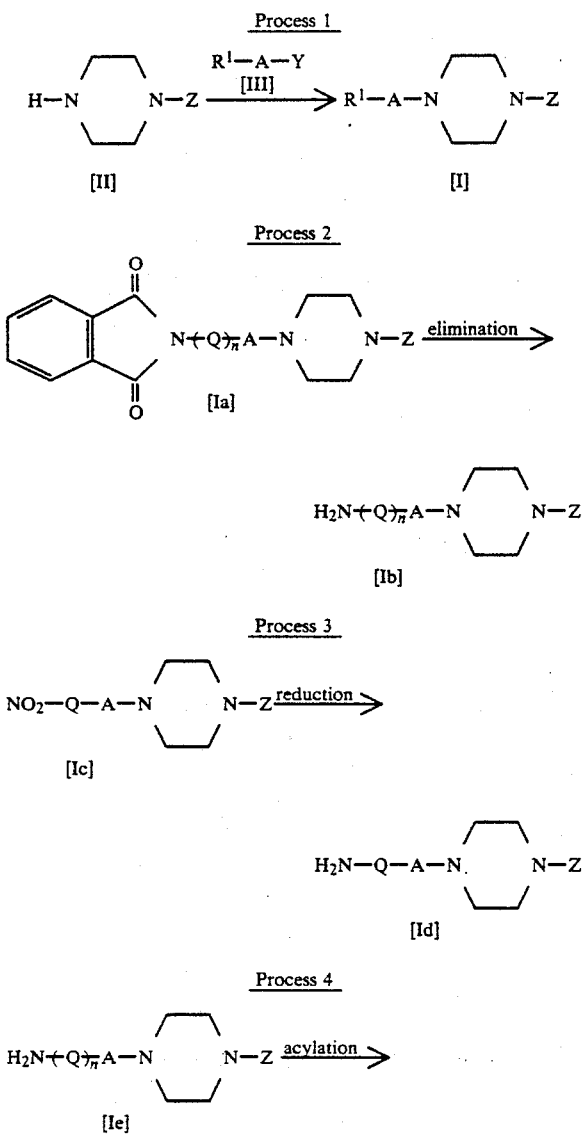

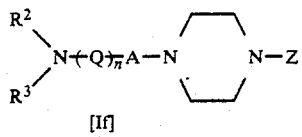

wherein
A, Z and $R^1$ are each as defined above,
Y is a leaving group,
Q is aryl or pyridyl,
n is an integer of 0 or 1,
$R^2$ is acyl, and
$R^3$ is hydrogen or acyl.

In the above formulas, the leaving group for Y may be halogeno [e.g. chloro, bromo, iodo, etc.], acyloxy [e.g. tosyloxy, mesyloxy, etc.] or the like.

The aryl group for Q and the acyl group for $R^2$ and $R^3$ can be referred to those as exemplified for before $R^1$, respectively.

The processes for preparing the object compounds [I] of this invention are explained in detail in the following.

PROCESS 1

The object compound [I] and its salt can be prepared by reacting a compound [II] or its salt with a compound [III] or its salt.

Suitable salts of the compounds [II] and [III] may be the same as those exemplified as salts of the object compound [I].

The reaction may be preferably carried out in the presence of an organic or an inorganic base. Suitable examples of the base may be tri(lower)alkylamine [e.g. trimethylamine, triethylamine, etc.], N,N-di(lower)alkylarylamine [e.g. N,N-dimethylaniline, etc.], N,N-di(lower)alkylar(lower)alkylamine [e.g. N,N-dimethylbenzylamine, etc.], pyridine, picoline, 1,5-diazabicyclo[4,3,0]-5-nonene, 1,4-diazabicyclo[2,2,2]octane, 1,5-diazabicyclo[5,4,0]-5-undecene, alkali metal acetate [e.g. sodium acetate, potassium acetate, etc.], alkali metal(lower)alkoxide [e.g. sodium methoxide, sodium ethoxide, potassium t-butoxide, etc.], alkali metal hydride [e.g. sodium hydride, potassium hydride, etc.], alkali metal hydroxide [e.g. sodium hydroxide, potassium hydroxide, etc.], alkaline earth metal hydroxide [e.g. magnesium hydroxide, calcium hydroxide, etc.], alkali metal carbonate [e.g. sodium carbonate, potassium carbonate, etc.], alkaline earth metal carbonate [e.g. magnesium carbonate, calcium carbonate, etc.], alkali metal bicarbonate [e.g. sodium bicarbonate, potassium bicarbonate, etc.] or the like.

This reaction is usually carried out in a solvent such as methanol, ethanol, propanol, dioxane, tetrahydrofuran, benzene, chloroform, dimethylformamide, dimethyl sulfoxide or any other solvent which does not adversely influence the reaction.

The reaction temperature is not critical, and the reaction is usually carried out under warming or heating.

PROCESS 2

The object compound [Ib] and its salt can be prepared by subjecting a compound [Ia] or its salt to elimination reaction of the phthaloyl group.

This reaction can be carried out in a conventional manner such as hydrolysis of the compound [Ia] or its salt, treatment of the compound [Ia] or its salt with ammonia or its derivative, or the like.

The hydrolysis is usually carried out in the presence of an acid catalyst such as inorganic acid [e.g. hydrochloric acid, hydrobromic acid, sulfuric acid, phosphoric acid, etc.], organic acid [e.g. methanesulfonic acid, benzenesulfonic acid, p-toluenesulfonic acid, etc.] or the like. This reaction is usually carried out in a solvent such as water or a mixture of water and organic solvent [e.g. methanol, ethanol, propanol, dimethyl sulfoxide, etc.] or the like. In case that the aforementioned acid is liquid, it can be also used as a solvent. The reaction temperature is not critical, and the reaction is usually carried out under warming or heating.

The ammonia derivative to be used in the treatment of the compound [Ia] with ammonia or its derivative may be lower alkylamine [e.g. methylamine, ethylamine, propylamine, etc.], hydrazine, hydrazine hydrate, phenylhydrazine or the like. This reaction is usually carried out in a solvent such as methanol, ethanol, propanol, tetrahydrofuran, dioxane, dimethylformamide or the like. The reaction temperature is not critical, and the reaction is usually carried out under warming or heating.

PROCESS 3

The object compound [Id] and its salt can be prepared by reducing the compound [Ic] or its salt.

This reaction can be carried out in a conventional method for reducing a nitro group to an amino group, for example, chemical reduction, catalytic reduction or the like.

Suitable reducing agents to be used in chemical reduction are a metal [e.g. tin, zinc, iron, etc.], or a combination of such metal and an inorganic or organic acid [e.g. hydrochloric acid, hydrobromic acid, formic acid, acetic acid, trifluoroacetic acid, p-toluenesulfonic acid, etc.].

Suitable catalysts to be used in catalytic reduction are conventional ones such as platinum catalysts [e.g. spongy platinum, platinum black, platinum oxide, etc.], palladium catalysts [e.g. spongy palladium, palladium black, collodial palladium, palladium on carbon, palladium on barium sulfate, etc.], nickel catalysts [e.g. Raney nickel, etc.] or the like.

The chemical reduction and catalytic reduction are usually carried out in a solvent such as water, methanol, ethanol, propanol, dioxane, tetrahydrofuran, diethyl ether or any other solvent which does not adversely influence the reaction. Additionally, in case that the aforementioned acid to be used in chemical reduction is liquid, it can be also used as a solvent.

The reaction temperature is not critical, and the reaction is usually carried out at ambient temperature or under warming.

PROCESS 4

The object compound [If] and its salt can be prepared by acylating a compound [Ie] or its salt.

Suitable acylating agents may include acids containing the acyl group as exemplified before and reactive derivatives thereof.

Suitable examples of the reactive derivative may be acid halide [e.g. acid chloride, acid bromide, etc.]; acid anhydride with lower alkanoic acid [e.g. acetic acid, etc.] or mono-(lower)alkylcarbonate [e.g. mono ethyl carbonate, etc.]; activated amide with pyrazole, imidazole, 4-methylimidazole or the like; activated ester [e.g. cyanomethyl ester, methoxymethyl ester, p-nitrophenyl ester, etc.] or the like.

This reaction can be carried out in the presence of an organic or inorganic base as exemplified in Process 1.

In case that a free acid is used as an acylating agent, the reaction is preferably conducted in the presence of a condensing agent. Suitable condensing agents may be carbodiimide compound [e.g. N,N-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.], keteneimine compound [e.g. N,N'-carbonylbis(2-methylimidazole), pentamethyleneketene-N-cyclohexylimine, diphenylketene-N-cyclohexylimine, etc.], olefinic or acetylenic ether compound [e.g. ethoxyacetylene, β-chlorovinylether ether, etc.], sulfonic acid ester of N-hydroxybenzotriazole derivatives [e.g. 1-(4-chlorobenzenesulfonyloxy)-6-chloro-1H-benzotriazole, etc.], phosphorus compound [e.g. trialkyl phosphite, ethyl polyphosphate, isopropyl polyphosphate, phosphoryl chloride, phosphorus trichloride, triphenylphosphine, etc.], thionyl chloride, oxalyl chloride, N-ethyl benzisoxazolium, N-ethyl-5-phenylisoxazolium-3'-sulfonate, so-called Vilsmeier reagent produced by the reaction of amide compound [e.g. dimethylformamide, diethylformamide, etc.] with halogenated compound [e.g. thionyl chloride, phosphoryl chloride, phosgene, etc.] or the like.

This reaction is usually carried out in a solvent such as methylene chloride, chloroform, ethylene chloride, acetone, methanol, ethanol, tetrahydrofuran, pyridine, dimethylformamide or any other solvent which does not adversely influence the reaction.

The reaction temperature is not critical, and the reaction is usually carried out under cooling or at ambient temperature.

The object compounds prepared by the abovementioned Processes 1 to 4 can be isolated and purified by a conventional manner.

The starting compounds [III] include novel compounds, and said compounds can be prepared by the following method.

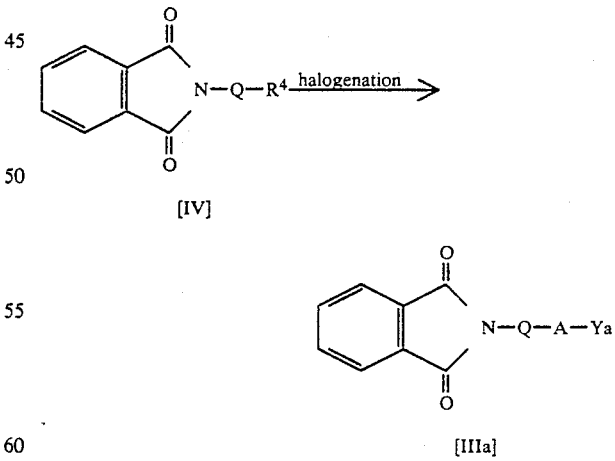

wherein
R[4] is lower alkyl,
Ya is halogen, and
Q and A are each as defined above.

In the above reaction scheme, the lower alkyl for R[4] and the halogen for Ya may be the same as those exemplified before, respectively.

The compound [IIIa] and its salt can be prepared by halogenating a compound [IV] or its salt.

Suitable salts of the compounds [IIIa] and [IV] may be the same as those exemplified as salts of the object compound [I].

The compound [IIIa] can be prepared according to Preparation 1 mentioned below or chemically analogous process thereto.

As being apparent from the following test results, the object compounds [I] obtained by the process of this invention and their salts possess antiallergic activity and are useful for antiallergic medicaments.

TEST METHOD (1) Preparation of rabbit antiserum against egg albumin

Equal volumes of a saline solution of egg albumin (200 mg/ml) and of Freund's Complete Adjuvant were mixed and emulsified. Each male New Zealand white strain rabbits, each weighing 2 to 2.5 kg., received an intramuscular injection of 0.5 ml of the emulsion in the left and right thigh regions. One week later, they received an intradermal injection of 0.25 ml of a saline solution of egg albumin (concentration: 20 mg/ml) in the different four sites of the dorsal skin surface three times every other week. Blood samples were collected from the carotid artery one week after the last injection.

(2) Determination of Passive Cutaneous Anaphylaxis (PCA) titer

The level of anaphylactic anti-egg albumin antibodies in pools of sera were determined by passive cutaneous anaphylaxis (PCA) reactions using shaven Hartley strain test guinea-pigs.

Antiserum was serially diluted (two fold) in saline and 0.1 ml of each antiserum dilution were injected intradermally into the dorsal skin surface of the test guinea-pigs. 24 hours after intradermal sensitization, Egg albumin-specific PCA reactions were elicited by intravenous injection of 10 mg of egg albumin in 1 ml of 1% Evans blue dye dissolved in saline. Reactions were read and recorded as the highest dilution of serum evoking threshold PCA reactivity (5 mm diameter).

(3) Antagonism to anaphylactic asthma in guinea-pigs

Male Hartley strain guinea-pigs, weighing 305 to 400 g, were used. Animals were sensitized by an intravenous injection of rabbit antiserum against egg albumin (4000 PCA titer) with 0.5 ml/animal. After 24 hours, animals were placed individually in a plastic chamber of 5.3 liter volume. An aerosol of 5% egg albumin solution was sprayed in the chamber at a rate of 0.16 ml/min with a commercial nebulizer. The test compounds were given to the animals orally 30 minutes before the challenge with the egg albumin solution. Each dose group consisted of 3 or 5 animals. The inhibitory effect of the test compounds was determined from the number of surviving animals more than 2 hours after spray of the antigen.

TEST RESULTS

Inhibitory effect of anaphylactic asthma in guinea-pig

| Test Compound (Example No.) | Inhibitory Effect (%) (Dose: 10 mg/kg) |
| --- | --- |
| Example 1 | 100 |
| Example 7 | 100 |
| Example 10-(2) | 80 |
| Example 10-(5) | 100* |

-continued

| Test Compound (Example No.) | Inhibitory Effect (%) (Dose: 10 mg/kg) |
| --- | --- |
| Example 10-(8) | 80 |
| Example 11 | 100* |
| Example 13 | 100 |

*Dose group: 3 guinea-pigs

As being apparent from the above test results, the object compounds [I] of the present invention possess antiallergic activity and are useful for medicines.

For inhibitive or therapeutic administration, the object compounds [I] of the present invention and salts thereof are used in a form of the conventional pharmaceutical preparation in admixture with a conventional pharmaceutically acceptable carrier such as an organic or inorganic, solid or liquid excipient which is suitable for oral, parenteral or external administration. The pharmaceutical preparation may be compounded in a solid form such as powder, granule, capsule, tablet, ointment or suppository, or in a liquid form such as solution, suspension or emulsion. If needed, there may be included in the above preparation stabilizing agent, wetting agent, suspending agent, emulsifying agent, buffer or any other commonly used additives.

The effective ingredient may usually be administered with a unit dose of 10 mg/kg to 500 mg/kg, 1 to 4 times a day. However, the above dosage may be increased or decreased according to age, weight and conditions of the patient or the administering method.

The following preparation and examples are given only for the purpose of illustrating the present invention in more detail.

PREPARATION 1

A mixture of N-(2-methylpyridin-6-yl)phthalimide (16.7 g), N-bromosuccinimide (15.0 g) and benzoyl peroxide (300 mg) in chloroform (150 ml) was refluxed for 5 hours with stirring under ultraviolet irradiation, and then additional N-bromosuccinimide (12.5 g) and benzoyl peroxide (300 mg) were added thereto. The mixture was further refluxed for 18 hours with stirring under ultraviolet irradiation. The reaction mixture was evaporated to dryness and the residue was extracted with ethyl acetate. The extract was washed with water, dried and evaporated to dryness. The residue was subjected to column chromatography on silica gel eluting with a mixed solvent (toluene:ethyl acetate=20:1) to give N-(2-bromomethylpyridin-6-yl)phthalimide (8.85 g). mp: 169°-170° C.

IR (Nujol): 1780, 1762, 1725, 1597, 1462, 1383, 1112, 889 cm$^{-1}$.

NMR (DMSO-d$_6$, δ): 4.75 (2H, s), 7.4–7.9 (2H, m), 7.9–8.3 (5H, m).

Analysis: Calcd. for $C_{14}H_9BrN_2O_2$. Calcd.: C 53.02, H 2.86, N 8.83. Found: C 53.19, H 2.75, N 8.87.

EXAMPLE 1

To a solution of 5-chloro-2-pentanone (1.21 g) and 1-benzhydrylpiperazine (2.52 g) in dimethylformamide (8 ml) was added powdered anhydrous potassium carbonate (0.828 g) and the mixture was stirred at 70° C. for 2.5 hours. The reaction mixture was poured into ice-water (50 ml) and extracted with ethyl acetate. The extract was washed with water, dried over magnesium sulfate and evaporated to give an oily product (3.3 g), which was subjected to column chromatography on silica gel (25 g) eluting with a mixture of chloroform and methanol (5:1). The fractions containing the desired compound were combined and evaporated in vacuo. According to a conventional manner, the residue was converted to fumaric acid salt, which was recrystallized from ethanol to give 1-(4-oxo-1-pentyl)-4-benzhydrylpiperazine fumarate (1.4 g) as white needles. mp: 186°–188.5° C.

IR (Nujol): 1702, 1632, 1203, 760, 712 cm$^{-1}$.

NMR (DMSO-d$_6$, δ): 1.2–2.1 (4H, m), 2.02 (3H, s), 2.1–3.0 (10H, m), 4.30 (1H, s), 6.59 (2H, s), 7.1–7.6 (10H, m), 9.02 (2H, s).

Analysis: Calcd. for $C_{22}H_{28}N_2O \cdot C_4H_4O_4$. Calcd.: C 69.00, H 7.13, N 6.19. Found: C 68.79, H 7.18, N 6.17.

EXAMPLE 2

A mixture of 3-nitrobenzylchloride (3.43 g), 1-benzhydrylpiperazine (5.04 g) and anhydrous potassium carbonate (2.76 g) in dimethylformamide (35 ml) was stirred at ambient temperature for 1.5 hours. The reaction mixture was poured into ice-water and extracted with ethyl acetate. The extract was washed with water, dried and evaporated in vacuo to give an oily product, which was subjected to column chromatography on silica gel eluting with a mixture of toluene and ethyl acetate (20:1). The fractions containing the desired compound were combined and evaporated in vacuo. According to a conventional manner, the residue was converted to fumaric acid salt, which was recrystallized from ethanol to give 1-(3-nitrobenzyl)-4-benzhydrylpiperazine fumarate (7.62 g) as colorless prisms. mp: 211°–212° C.

IR (Nujol): 3610, 3340, 1740, 1640, 1575, 1350, 760 cm$^{-1}$.

NMR (DMSO-d$_6$, δ): 2.1–2.8 (8H, m), 3.70 (2H, s), 4.31 (1H, s), 6.68 (2H, s), 6.9–7.9 (12H, m), 7.9–8.3 (2H, m), 9.83 (2H, m).

Analysis: Calcd. for $C_{24}H_{25}N_3O_2 \cdot C_4H_4O_4$. Calcd.: C 66.79, H 5.81, N 8.35. Found: C 65.94, H 5.71, N 8.23.

EXAMPLE 3

A mixture of N-(3-bromopropyl)phthalimide (5.35 g), 1-benzhydrylpiperazine (5.0 g) and anhydrous potassium carbonate (2.8 g) in dimethylformamide (20 ml) was stirred at 65° C. for 100 minutes. The reaction mixture was evaporated in vacuo and water was added thereto. The crystalline precipitate was collected by filtration and dried. The crystalline product was dissolved in methanol (200 ml) and to the solution was introduced hydrogen chloride for 20 minutes under cooling. The crystalline precipitate was collected by filtration and recrystallized from methanol to give 1-(3-phthalimidopropyl)-4-benzhydrylpiperazine dihydrochloride (7.0 g) as white crystals. mp: 238°–240° C.

IR (Nujol): 2400–2800, 1765, 1710, 715 cm$^{-1}$.

NMR (DMSO-d$_6$, δ): 2.05 (2H, broad), 3.4–3.70 (12H, broad), 5.61 (1H, broad), 7.30–7.80 (16H, m).

Analysis: Calcd. for $C_{28}H_{29}N_3O_2 \cdot 2HCl$. Calcd.: C 65.04, H 6.13, N 8.12. Found: C 65.08, H 5.92, N 8.04.

EXAMPLE 4

A mixture of N-(3-bromopropyl)phthalimide (26.8 g), 1-(4-chlorobenzhydryl)piperazine (28.6 g) and anhydrous potassium carbonate (13.8 g) in dimethylformamide (150 ml) was stirred at 70° C. for 2.5 hours. After being cooled to ambient temperature, the reaction mixture was poured into ice-water. The crystalline precipitate was collected by filtration, dried and dissolved in ethanol (800 ml). To the solution was added hydrazine hydrate (11.0 g) and the mixture was refluxed for 20 hours. The reaction mixture was hot-filtered and stood to cool. The obtained crystal was suspended in 10% hydrochloric acid (500 ml). The suspension was filtered and the filtrate was concentrated. The resultant residue was neutralized with aqueous sodium carbonate and extracted with chloroform. The extract was washed with water, dried and evaporated in vacuo to give 1-(3-aminopropyl)-4-(4-chlorobenzhydryl)piperazine (35.0 g) as an oil.

EXAMPLE 5

A mixture of N-(2-bromomethylpyridin-6-yl)phthalimide (6.9 g), 1-benzhydrylpiperazine (5.5 g) and anhydrous potassium carbonate (1.65 g) in dimethylformamide was stirred at 60° C. for 2 hours. The reaction mixture was poured into ice-water, and the crystalline precipitate was collected by filtration and dried to give white crystal (10.9 g). The crystal was dissolved in a mixture of methanol (40 ml) and hydrochloric acid (40 ml) and the solution was refluxed for 2 hours. The reaction mixture was concentrated and the resultant residue was neutralized with aqueous potassium carbonate and extracted with ethyl acetate. The extract was washed with water, dried and evaporated in vacuo. The residue was crystallized from diethyl ether to give 1-(6-aminopyridin-2-ylmethyl)-4-benzhydrylpiperazine (3.9 g). mp: 144°–145° C.

IR (Nujol): 3460, 3310, 1638, 1598, 1469, 1330, 1005, 790, 756, 705 cm$^{-1}$.

NMR (CDCl$_3$, δ): 2.50 (8H, s), 3.49 (2H, s), 4.26 (1H, s), 4.46 (2H, broad), 6.30 (1H, d, J=8.0 Hz), 6.68 (1H, d, J=8.0 Hz), 7.05–7.70 (11H, m).

Analysis: Calcd. for $C_{23}H_{26}N_4$. Calcd.: C 77.06, H 7.31, N 15.63. Found: C 77.24, H 7.26, N 15.58.

EXAMPLE 6

An oil of 1-(3-nitrobenzyl)-4-benzhydrylpiperazine, obtained by neutralizing of its fumarate (7.05 g) with aqueous potassium carbonate and extracting with ethyl acetate, was dissolved in a mixture of ethanol (55 ml) and tetrahydrofuran (10 ml). The solution was hydrogenated in the presence of 10% palladium charcoal (0.7 g) under an atmospheric pressure of hydrogen. After removal of the catalyst by filtration, the filtrate was evaporated in vacuo. The oily residue was pulverized in a mixture of diethyl ether and hexane to give powder, which was recrystallized from ethanol to afford 1-(3-aminobenzyl)-4-benzhydrylpiperazine (4.7 g) as colorless prisms. mp: 104.5°–106.5° C.

IR (Nujol): 3410, 3300, 3200, 1605, 1448, 1372, 1158, 1003, 760 cm$^{-1}$.

NMR (CDCl$_3$, δ): 2.40 (8H, s), 3.38 (4H, s), 4.20 (1H, s), 6.3–6.8 (3H, m), 6.8–7.6 (11H, m).

Analysis: Calcd. for $C_{24}H_{27}N_3$. Calcd.: C 80.63, H 7.61, N 11.75. Found: C 80.51, H 7.75, N 11.86.

EXAMPLE 7

To a solution of 1-(3-aminopropyl)-4-benzhydrylpiperazine (1.2 g) in a mixture of pyridine (2 ml) and chloroform (15 ml) was dropwise added a solution of benzoyl chloride (0.55 ml) in chloroform (3 ml) at ambient temperature with stirring, which was continued for 1.5 hours. The reaction mixture was washed successively with aqueous sodium bicarbonate and water. The chloroform layer was separated, dried and evaporated in vacuo to give an oil. According to a conventional manner, the oil was converted to hydrochloric acid salt, which was recrystallized from a mixture of methanol and diethyl ether to afford 1-(3-benzoylaminopropyl)-4-benzhydrylpiperazine dihydrochloride (1.0 g) as white crystals. mp: 235°–237° C.

IR (Nujol): 3300, 2400, 1660, 710 cm$^{-1}$.

NMR (DMSO-d$_6$, δ): 2.02 (2H, broad), 3.40–3.50 (8H, broad), 3.75 (4H, broad), 5.81 (1H, broad), 7.50–8.00 (15H, m), 8.75 (1H, t), 12.00 (2H, broad).

Analysis: Calcd. for $C_{27}H_{31}N_3O.2HCl$. Calcd.: C 66.65, H 6.83, N 8.64. Found: C 66.16, H 6.85, N 8.60.

EXAMPLE 8

To a solution of 1-(3-aminopropyl)-4-(4-chlorobenzhydryl)piperazine (1.7 g) and triethylamine (0.7 g) in chloroform (20 ml) was dropwise added benzoyl chloride (0.7 ml) at ambient temperature and the mixture was stirred at the same temperature for 1.5 hours. The reaction mixture was washed successively with aqueous sodium bicarbonate and water, and then extracted with 10% hydrochloric acid. After neutralizing the aqueous extract with aqueous sodium carbonate, the desired product was extracted with ethyl acetate. The organic extract was washed with water, dried and evaporated in vacuo to give an oil. According to a conventional manner, the oily product was converted to fumaric acid salt, which was recrystallized from a mixture of ethanol and diethyl ether to afford 1-(3-benzoylaminopropyl)-4-(4-chlorobenzhydryl)piperazine fumarate (0.82 g) as white crystals. mp: 173°–175° C. (dec.).

IR (Nujol): 3320, 2300–2600, 1690, 1630, 1570, 760 cm$^{-1}$.

NMR (DMSO-d$_6$, δ): 1.66 (2H, broad), 2.55 (10H, m), 3.30 (2H, m), 4.33 (1H, s), 6.59 (2H, s), 7.3–7.8 (14H, m), 8.15 (2H, broad), 8.55 (1H, broad).

Analysis: Calcd. for $C_{27}H_{30}ClN_3O.C_4H_4O_4$. Calcd.: C 66.00, H 6.07, N 7.45. Found: C 66.11, H 6.06, N 7.39.

EXAMPLE 9

To a solution of 1-(3-aminopropyl)-4-benzhydrylpiperazine (1.55 g) and triethylamine (0.7 ml) in chloroform (15 ml) was dropwise added p-methoxybenzoyl chloride (0.85 g) at ambient temperature with stirring, which was continued for 20 minutes. The reaction mixture was washed successively with aqueous sodium bicarbonate and water. The organic layer was separated, dried and evaporated in vacuo. The resultant oily product was subjected to column chromatography on silica gel eluting with ethyl acetate. The fractions containing the desired compound were combined and evaporated in vacuo. The residue was crystallized from a mixture of ethyl acetate and hexane to give 1-[3-(4-methoxybenzoylamino)propyl]-4-benzhydrylpiperazine (1.1 g) as white crystals. mp: 126°–128° C.

IR (Nujol): 3240, 1615, 1600, 1540, 1250, 745, 705 cm$^{-1}$.

NMR (DMSO-d$_6$, δ): 1.60 (2H, m), 2.1–2.4 (10H, m), 3.25 (2H, m), 3.72 (3H, s), 4.20 (1H, s), 6.89 (2H, d, J=9.0 Hz), 7.74 (2H, d, J=9.0 Hz), 7.1–7.40 (10H, m), 8.20 (1H, t).

Analysis: Calcd. for $C_{28}H_{33}N_3O_2$. Calcd.: C 75.82, H 7.50, N 9.47. Found: C 75.99, H 7.53, N 9.54.

EXAMPLE 10

The following compounds were obtained according to substantially the same manner as that of Example 9.

(1) 1-[3-(3-Methoxybenzoylamino)propyl]-4-benzhydrylpiperazine dihydrochloride. mp: 227°–230° C. (dec.)

IR (Nujol): 3310, 2300–2600, 1655, 1600, 1580, 760 cm$^{-1}$.

NMR (DMSO-d$_6$, δ): 2.00 (2H, broad), 2.1–3.5 (8H, broad), 3.6–3.7 (4H, broad), 3.84 (3H, s), 5.68 (1H, broad), 7.1–8.0 (14H, m), 8.76 (1H, broad).

Analysis: Calcd. for $C_{28}H_{33}N_3O_2.2HCl$. Calcd.: C 65.11, H 6.83, N 8.13. Found: C 65.25, H 7.00, N 8.14.

(2) 1-[3-(2-Methoxybenzoylamino)propyl]-4-benzhydrylpiperazine dihydrochloride. mp: 165°–180° C. (dec.)

IR (Nujol): 3380, 3210, 2300–2600, 1655, 1595, 760, 705 cm$^{-1}$.

NMR (DMSO-d$_6$, δ): 2.00 (2H, broad), 3.00–3.80 (12H, m), 3.86 (3H, s), 5.55 (1H, broad), 6.9–7.9 (14H, m), 8.25 (1H, broad).

Analysis: Calcd. for $C_{28}H_{33}N_3O_2.2HCl$. Calcd.: C 65.11, H 6.83, N 8.13. Found: C 65.29, H 6.94, N 8.01.

(3) 1-[3-(4-Chlorobenzoylamino)propyl]-4-benzhydrylpiperazine. mp: 164°–166° C.

IR (Nujol): 3270, 1650, 1630, 1595, 1560, 840, 760 cm$^{-1}$.

NMR (DMSO-d$_6$, δ): 1.66 (2H, m), 2.43–2.56 (10H, m), 3.23 (2H, m), 4.25 (1H, s), 7.15–7.60 (10H, m), 7.53 (2H, d, J=9.0 Hz), 7.89 (2H, d, J=9.0 Hz), 8.54 (1H, m).

Analysis: Calcd. for $C_{27}H_{30}ClN_3O$. Calcd.: C 72.39, H 6.75, N 9.38. Found: C 72.19, H 6.85, N 9.35.

(4) 1-[3-(2-Methylbenzoylamino)propyl]-4-benzhydrylpiperazine. mp: 142°–145° C.

IR (Nujol): 3290, 1625, 1540, 1150, 750, 710 cm$^{-1}$.

NMR (DMSO-d$_6$, δ): 1.66 (2H, m), 2.3–2.6 (13H, m), 3.24 (2H, m), 4.30 (1H, s), 7.15–7.65 (14H, m), 8.26 (1H, broad).

Analysis: Calcd. for $C_{28}H_{33}N_3O$. Calcd.: C 78.65, H 7.78, N 9.83. Found: C 78.39, H 7.63, N 9.71.

(5) 1-[3-(2-Methanesulfonylaminobenzoylamino)propyl]-4-benzhydrylpiperazine dihydrochloride. mp: 220°–228° C. (dec.)

IR (Nujol): 3240, 2380, 1630, 1325, 1145, 760, 700 cm$^{-1}$.

NMR (DMSO-d$_6$, δ): 1.98 (2H, m), 3.06 (3H, s), 3.10–3.75 (12H, m), 5.45 (1H, broad), 7.1–7.9 (14H, m), 9.00 (1H, broad).

Analysis: Calcd. for $C_{28}H_{34}N_4O_3S.2HCl$. Calcd.: C 58.02, H 6.26, N 9.66. Found: C 57.62, H 6.27, N 9.53.

(6) 1-(3-Cinnamoylaminopropyl)-4-benzhydrylpiperazine dihydrochloride. mp: 170°–213° C.

IR (Nujol): 3280, 2300–2600, 1675, 1660, 1620, 1545, 760, 705 cm$^{-1}$.

NMR (DMSO-d$_6$, δ): 1.92 (2H, broad), 3.10–3.50 (8H, broad), 3.6–3.75 (4H, broad), 5.60 (1H, broad), 6.70 (1H, d, J=16.0 Hz), 7.2–8.0 (16H, m), 8.46 (1H, broad).

Analysis: Calcd. for $C_{29}H_{33}N_3O.2HCl.1/3H_2O$. Calcd.: C 67.17, H 6.93, N 8.10, H$_2$O 1.15. Found: C 66.94, H 7.17, N 7.84, H$_2$O 1.21.

(7) 1-[3-(3,4-Dimethoxycinnamoylamino)propyl]-4-benzhydrylpiperazine dihydrochloride. mp: 175°–190° C. (dec.)

IR (Nujol): 3280, 2400–2500, 1660, 1615, 1595, 765 cm$^{-1}$.

NMR (DMSO-d$_6$, δ): 1.92 (2H, broad), 3.40 (10H, broad), 3.68 (2H, broad), 3.84 (6H, s), 6.64 (1H, d, J=16.0 Hz), 7.14 (1H, d, J=16.0 Hz), 7.2–8.0 (13H, m), 8.34 (1H, broad).

Analysis: Calcd. for $C_{31}H_{37}N_3O_3.2HCl.1/3H_2O$. Calcd.: C 64.35, H 6.90, N 7.26, $H_2O$ 1.03. Found: C 63.90, H 6.82, N 7.16, $H_2O$ 0.96.

(8) 1-[3-[2-(2-Oxo-benzothiazolin-3-yl)acetylamino]-propyl]-4-benzhydrylpiperazine. mp: 170°–182° C.

IR (Nujol): 3240, 1685, 1670, 1650, 1590, 1570, 755 $cm^{-1}$.

NMR (DMSO-$d_6$, δ): 1.50 (2H, m), 2.3–2.6 (10H, m), 3.03 (2H, m), 4.18 (1H, s), 4.46 (2H, s), 6.95–7.7 (14H, m), 8.13 (1H, broad).

Analysis: Calcd. for $C_{29}H_{32}N_4O_2S$. Calcd.: C 69.57, H 6.44, N 11.19. Found: C 69.81, H 6.50, N 11.18.

(9) 1-(3-Methanesulfonylaminopropyl)-4-benzhydryl-piperazine. mp: 115°–117° C.

IR (Nujol): 1595, 1320, 1145, 1000, 705 $cm^{-1}$.

NMR (DMSO-$d_6$, δ): 1.56 (2H, m), 2.50 (10H, m), 2.89 (3H, s), 3.00 (2H, t, J=6.0 Hz), 4.34 (1H, s), 7.11 (1H, t, J=6.0 Hz), 7.30–7.70 (10H, m).

Analysis: Calcd. for $C_{21}H_{29}N_3O_2S$. Calcd.: C 65.08, H 7.54, N 10.84. Found: C 65.33, H 7.65, N 10.86.

EXAMPLE 11

A mixture of 1-(3-aminopropyl)-4-benzhydrylpiperazine (1.55 g) and acetic anhydride (16 ml) was stirred at 100° C. for 1.5 hours. The reaction mixture was concentrated and the residue was extracted with ethyl acetate. The extract was washed successively with aqueous sodium bicarbonate and water, dried and evaporated in vacuo. The residue was purified by column chromatography on silica gel eluting with ethyl acetate. The fractions containing the desired compound were combined and evaporated in vacuo to give a residue. According to a conventional manner, the residue was converted to a hydrochloric acid salt, which was recrystallized from a mixture of methanol and diethyl ether to afford 1-(3-acetylaminopropyl)-4-benzhydrylpiperazine (0.8 g) as white crystals. mp: 240°–255° C. (dec.)

IR (Nujol): 3270, 2400, 1660, 1550, 910, 705 $cm^{-1}$.

NMR (DMSO-$d_6$, δ): 1.66 (3H, s), 1.70–1.90 (2H, m), 2.9–3.7 (12H, m), 5.55 (1H, broad), 7.20–8.10 (10H, m).

Analysis: Calcd. for $C_{22}H_{29}N_3O.2HCl$. Calcd.: C 62.26, H 7.36, N 9.90. Found: C 62.22, H 7.34, N 9.86.

EXAMPLE 12

To a solution of 1-(3-aminobenzyl)-4-benzhydrylpiperazine (1.43 g) in a mixture of pyridine (3.2 g) and chloroform (20 ml) was dropwise added methanesulfonylchloride (0.31 ml) at 5° to 6° C. with stirring. The mixture was stirred at the same temperature for 30 minutes and at ambient temperature for 2 hours. The reaction mixture was concentrated and the resultant was extracted with ethyl acetate. The extract was washed with water, dried and evaporated in vacuo to give a residue. According to a conventional manner, the residue was converted to fumarate, which was recrystallized from ethanol to afford 1-(3-methanesulfonylaminobenzyl)-4-benzhydrylpiperazine fumarate (0.65 g) as yellow crystals. mp: 213°–215° C.

IR (Nujol): 3230, 1690, 1640, 1590, 1330, 1255, 1200, 1140, 970, 760, 710 $cm^{-1}$.

NMR (DMSO-$d_6$, δ): 1.90–2.70 (8H, m), 2.96 (3H, s), 3.59 (2H, s), 4.30 (1H, s), 5.55 (3H, broad), 6.64 (2H, s), 6.80–7.50 (14H, m).

Analysis: Calcd. for $C_{25}H_{29}N_3O_2S.C_4H_4O_4$. Calcd.: C 63.14, H 6.03, N 7.62. Found: C 63.50, H 5.91, N 7.64.

EXAMPLE 13

To a solution of 1-(6-aminopyridin-2-ylmethyl)-4-benzhydrylpiperazine (3.58 g) and triethylamine (1.01 g) in chloroform (20 ml) was dropwise added methanesulfonylchloride (1.15 g) at 5° to 10° C. under cooling with stirring, which was continued at the same temperature for 1 hour. To the resultant mixture, additional triethylamine (0.51 g) and methanesulfonyl chloride (0.57 g) were added successively. The mixture was stirred for 1.5 hours. The reaction mixture was washed with water, dried and evaporated in vacuo. The resulting oily product was subjected to column chromatography on silica gel eluting with a mixture of chloroform and methanol (30:1). The fractions containing the desired compound were combined and evaporated in vacuo to give a residue. According to a conventional manner, the residue was converted to hydrochloric acid salt, which was recrystallized from a mixture of methanol and diethyl ether to give 1-(6-methanesulfonylaminopyridin-2-ylmethyl)-4-benzhydrylpiperazine dihydrochloride (0.97 g). mp: 201°–202° C.

IR (Nujol): 3400, 3210, 2480, 2400, 1595, 1579, 1453, 1443, 1328, 1126, 972, 944, 749, 706 $cm^{-1}$.

NMR (DMSO-$d_6$, δ): 3.15 (3H, s), 3.37 (4H, m), 3.75 (4H, m), 4.48 (2H, m), 5.65 (1H, broad), 6.96 (1H, d, J=8.0 Hz), 7.35 (8H, m), 7.81 (4H, m).

Analysis: Calcd. for $C_{24}H_{28}N_4O_2S.2HCl.H_2O$. Calcd.: C 54.52, H 6.13, N 10.59, $H_2O$ 3.41. Found: C 54.47, H 6.25, N 10.58, $H_2O$ 3.62.

EXAMPLE 14

1-[6-(N,N-Dimethanesulfonylamino)pyridin-2-ylmethyl]-4-benzhydrylpiperazine was obtained according to substantially the same manner as that of Example 13. mp: 167°–169° C.

IR (Nujol): 1596, 1448, 1360, 1347, 1320, 1160, 1149, 1002, 960, 932, 908, 767, 758, 703 $cm^{-1}$.

NMR (CDCl$_3$, δ): 2.49 (8H, m), 3.54 (6H, s), 3.66 (2H, s), 4.24 (1H, s), 7.05–7.90 (3H, m).

Analysis: Calcd. for $C_{25}H_{30}N_4O_4S_2$. Calcd.: C 58.34, H 5.88, N 10.89. Found: C 58.32, H 5.90, N 10.67.

What we claim is:

1. A compound of the formula:

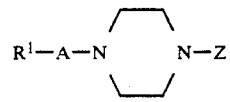

wherein

A is a lower alkylene group,

Z is a benzhydryl group optionally substituted with a halogen atom, and $R^1$ is (1) a pyridyl group substituted with a lower alkanesulfonylamino or di(lower alkanesulfonyl)amino group; (2) a lower alkanoylamino group optionally substituted with 2-oxo-benzothiazolin-3-yl; (3) a lower alkane sulfonylamino group; or (4) a phenyl(lower)alkanoylamino group optionally substituted with two lower alkoxy groups;

and its pharmaceutically acceptable salts.

2. The compound of claim 1, wherein $R^1$ is a pyridyl group substituted with a lower alkanesulfonylamino or a di(lower alkane sulfonyl)amino group.

3. The compound of claim 2, wherein $R^1$ is a pyridyl group substituted with a lower alkanesulfonylamino group.

4. The compound of claim 1, wherein $R^1$ is a lower alkanoylamino group optionally substituted with 2-oxobenzothiazolin-3-yl; a lower alkane sulfonylamino group; or a phenyl(lower)alkanoylamino group optionally substituted with two lower alkoxy groups.

5. The compound of claim 4, wherein $R^1$ is a lower alkanoylamino group optionally substituted with 2-oxobenzothiazolin-3-yl.

6. The compound of claim 4, wherein $R^1$ is a lower alkanesulfonylamino group.

7. The compound of claim 4, wherein $R^1$ is a phenyl(lower)alkanoylamino group optionally substituted with two lower alkoxy groups.

8. A pharmaceutical composition comprising a compound of claim 1, as an effective ingredient, in association with a pharmaceutically acceptable, substantially nontoxic carrier or excipient.

9. A method for treatment of allergic symptoms which comprises administering a compound of claim 1 to human beings and animals.

* * * * *